United States Patent [19]

Wojtowicz et al.

[11] 4,360,671

[45] Nov. 23, 1982

[54] PREPARATION OF CYANURIC ACID

[75] Inventors: John A. Wojtowicz, Cheshire; Douglas A. Farmer, Jr., Madison, both of Conn.

[73] Assignee: Olin Corporation, New Haven, Conn.

[21] Appl. No.: 308,635

[22] Filed: Oct. 5, 1981

[51] Int. Cl.$^3$ ............................................. C07D 251/32
[52] U.S. Cl. ..................................................... 544/192
[58] Field of Search ......................................... 544/192

[56] References Cited

U.S. PATENT DOCUMENTS

| | | | |
|---|---|---|---|
| 2,952,679 | 9/1960 | Perret, Jr. | 260/248 |
| 3,065,233 | 11/1962 | Hopkins et al. | 260/248 |
| 3,117,968 | 1/1964 | Merkel et al. | 260/248 |
| 3,164,591 | 1/1965 | Walles et al. | 260/248 |
| 3,563,987 | 2/1971 | Berkowitz | 260/248 |
| 3,635,968 | 1/1972 | Goelz et al. | 260/248 A |
| 3,810,891 | 5/1974 | Lee | 260/248 A |

*Primary Examiner*—John M. Ford
*Attorney, Agent, or Firm*—Arthur E. Oaks; Donald F. Clements

[57] ABSTRACT

A highly pure cyanuric acid produced by pyrolyzing a nitrogenous containing material capable of yielding cyanuric acid, such as urea, in an alkyl dinitrile solvent such as adiponitrile, at elevated temperatures, is disclosed. The overall process converts substantially all of the urea to cyanuric acid and cyanuric acid derivatives which are capable of being converted into trichloroisocyanuric acid and similar compounds, while allowing substantially complete recovery of the nitrile solvent for reuse.

23 Claims, 3 Drawing Figures

PREPARATION OF CYANURIC ACID

BACKGROUND OF THE INVENTION

This invention relates to a novel process for producing cyanuric acid by pyrolytic conversion of a nitrogenous material such as urea.

It is known that cyanuric acid can be produced by the pyrolysis of urea. This reaction may be expressed by the equation:

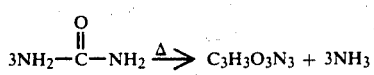

The resulting product, cyanuric acid, which has the emperical formula $C_3H_3O_3N_3$, is generally represented structurally either as:

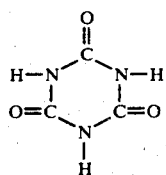

or

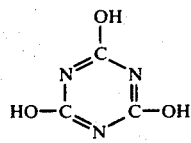

The pyrolysis can be carried out either in a dry state, that is, in the absence of a solvent, such as described in U.S. Pat. No. 2,943,088, issued to R. H. Westfall on June 28, 1960, or in the presence of various inert organic solvents, such as described in the U.S. Pat. Nos. 2,952,679, issued to Perret on Sept. 13, 1960 (dipropylene glycol); 3,065,223, issued to Hopkins et al on Nov. 20, 1962 (alkyl sulfones); 3,117,968, issued to Merkel et al on Jan. 14, 1974 (diphenyl); 3,164,591, issued to Walles et al on Jan. 5, 1965 (oxyzolidinones); 3,563,987, issued to Berkowitz on Feb. 16, 1971 (sulfolane); 3,635,968, issued to Goelz et al on Jan. 18, 1972 (N-cyclohexyl pyrrolidone); or 3,810,891, issued to Lee on May 14, 1974 (glycol ethers).

Unfortunately, the pyrolysis and condensation of urea to form cyanuric acid is not a unique reaction. Rather, a range of products, in addition to cyanuric acid, can be produced. These products may include amino substituted cyanuric acids, commonly referred to as amides of cyanuric acid, namely ammelide, ammeline, and melamine, as well as other undesirable side products, such as ammonium carbamate and other condensation products.

Furthermore, if careful control is not exercised in producing cyanuric acid by pyrolyzing the urea, numerous side products can be produced. In addition, it is difficult to obtain an easily handled end product in good yield and in a purified form. Where the cyanuric acid is to be chlorinated, it is essential, if satisfactory chlorinated cyanuric acids are to be obtained, that a relatively pure cyanuric acid be used as the starting raw material.

In order to obtain such a purified cyanuric acid, it is the custom in the art to treat crude cyanuric acid to an acid digestion in a strong acid media, e.g., 3 to 15 percent sulfuric or hydrochloric acid. This treatment selectively hydrolyzes the acid soluble ammelide and ammeline and converts them to cyanuric acid. In general, an acid digestion step is required where the concentration of ammeline or ammelide exceeds about 2 percent by weight of the cyanuric acid product.

SUMMARY OF THE INVENTION

It is an object of the present invention to provide a lower cost process in which urea is converted selectively to cyanuric acid containing minimal amounts of impurities.

It is a further object of the present invention to provide a process that produces cyanuric acid in a highly purified state, substantially free of cyanuric acid amides, so that acid digestion of the cyanuric acid product is not required.

It is yet a further object of the present invention to describe a process which converts urea to cyanuric acid in high yields and from which the cyanuric acid can be recovered readily.

These and other objects of the invention will become apparent from the following description and the appended claims.

It has now been found that the foregoing objects are accomplished in a process in which a nitrogenous material such as urea is converted selectively to cyanuric acid with minimal amounts of cyanuric acid amides by heating it in an alkyl dinitrile solvent such as adiponitrile to temperatures of at least 180° C. Adiponitrile readily dissolves the urea but only limited amounts of cyanuric acid which is readily extracted from the reaction mass by a variety of separation techniques.

DESCRIPTION OF THE INVENTION

Figure 1:
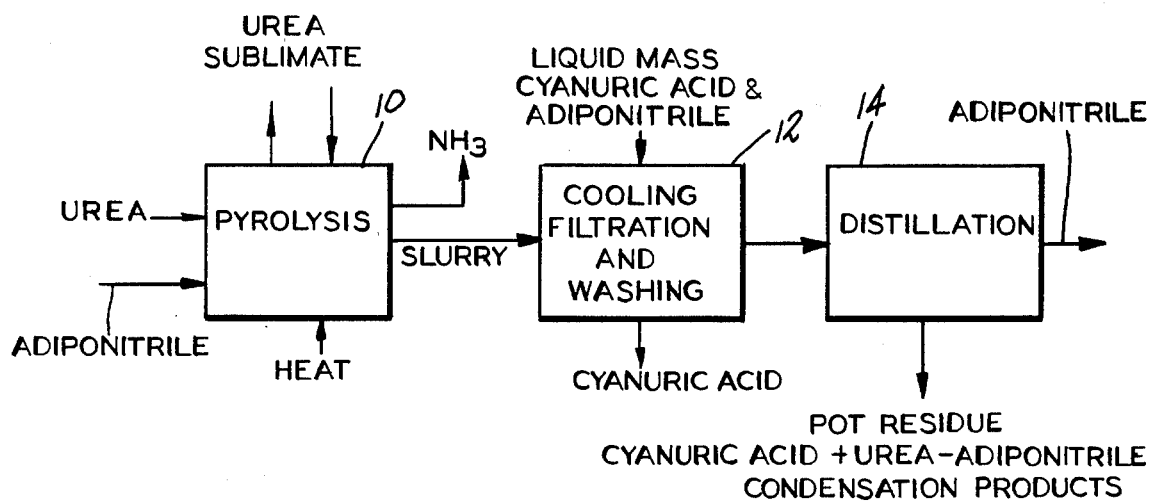
FIG. 1 is a flow diagram of a first embodiment of the subject invention, utilizing filtration to recover the cyanuric acid product.
Figure 3:
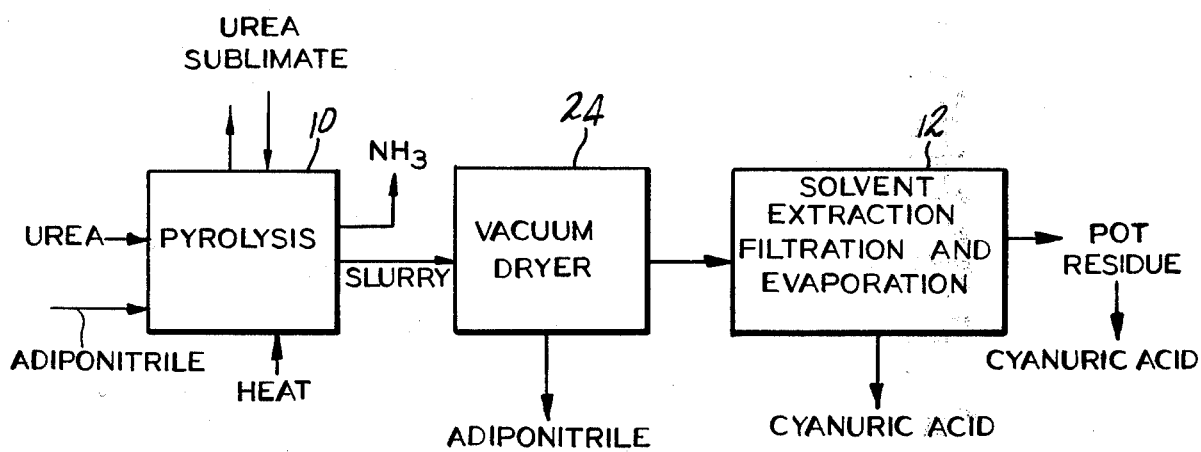
FIG. 3 is a flow diagram of a third embodiment of the subject invention, utilizing distillation to recover the cyanuric acid product.
Figure 2:
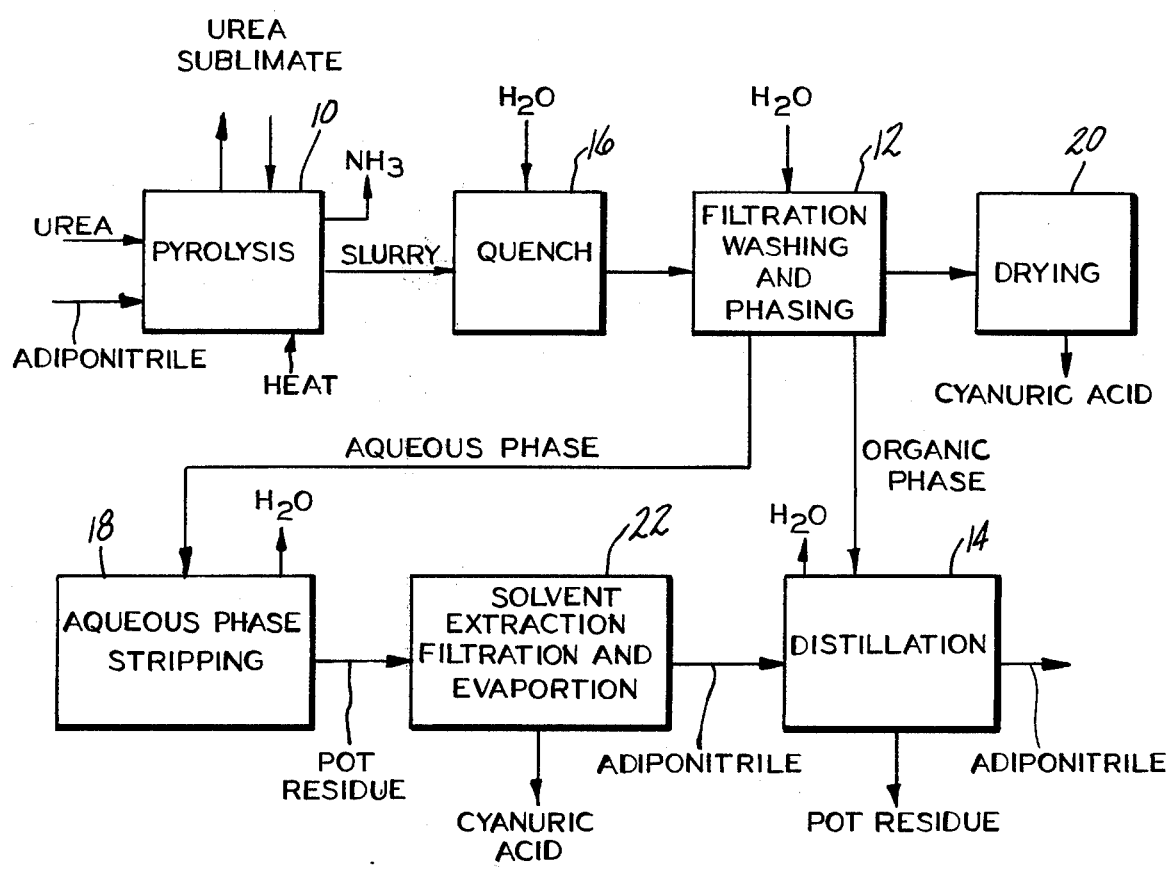
FIG. 2 is a flow diagram of a second embodiment of the subject invention, utilizing cooling and solvent extraction to recover the cyanuric acid product.

FIGS. 1-3 show three different methods for producing and recovering crude cyanuric acid from a reaction mass produced by pyrolyzing urea dissolved in a generally non-reactive linear alkyl dinitrile solvent, of the form $N{\equiv}C-(CH_2)_n-C{\equiv}N$, wherein n ranges from 'to 8, having a boiling point range of from 200°-350° C. at atmospheric pressure. Suitable solvents for this process include malononitrile, succinonitrile, glutaronitrile, adiponitrile, pimelonitrile, and the monomethyl derivatives thereof with adiponitrile being preferred. This is capable of dissolving urea in substantial quantities with the final product, cyanuric acid, being relatively insoluble therein. The invention will be defined hereinafter with adiponitrile being used to illustrate the use of any of the aforesaid linear alkyl dinitrile solvents.

In the process of this invention, the urea is gradually added, preferably in the form of prills having a minimum of "fines" or other powdery material, or as a molten stream to a heated pyrolysis vessel 10 containing adiponitrile heated to a temperature of at least 180° C.

and preferably to a temperature in the range of about 200° C. to 250° C. The urea is charged in an amount to provide a solvent to urea weight ratio of from about 0.5:1 to about 2:1 and preferably from about 0.9:1 to about 1.5:1. The urea is added at a uniform rate over a period of about 1 to 4 hours with the time of addition being a function of the operating conditions. In relatively small laboratory operation, a shorter addition time of about 1 to about 2 hours can be used whereas in a production environment, a longer addition time in the range of about 3 to 4 hours would normally be used. At the end of this time, the reaction mass comprises a hot slurry of about 25 to about 60 percent and preferably about 30 to about 50 percent by weight of crude cyanuric acid suspended in liquid adiponitrile.

The condensation reaction produced by pyrolysis is endothermic so that this rate of addition smooths out and simplifies the problem of providing the heat needed to start and maintain the condensation reaction. Further, by keeping the instantaneous concentration of urea low at all times, the condensation to cyanuric acid tends to proceed quickly and smoothly with essentially all of the urea reacting and with a minimum of unwanted by-products being produced. In so doing, the formation and emission of $NH_3$ occurs at a steady rate. Such a situation permits significant economies in the design and implementation of any units which might be used to recover this valuable by-product.

The pyrolysis and condensation reaction described above can be performed under subatmospheric, atmospheric and superatmospheric pressure conditions. Each mode of operation offers particular advantages and disadvantages and the use of any one of them is within the ambit of this invention. With subatmospheric pressure operation, generally in the range of 250 to 350 torr, the ease of removing or purging the by-product ammonia from the pyrolysis vessel is greatly enhanced. This serves to drive the condensation reaction to completion while minimizing the tendency to produce unwanted by-products. Thus, a highly selective conversion of urea to cyanuric acid occurs. At these conditions of temperature and pressure, the combined amount of ammelide or ammeline which is produced in the final reaction product is normally no greater than about 1 percent and is usually much less. Furthermore, the conversion of urea to cyanuric acid is substantially complete with total yields as high as 97 percent by weight or higher being obtainable. However, at subatmospheric pressure, the relatively high vapor pressure of urea at the pyrolysis temperature results in a significant amount of urea sublimation. In an industrial process where the system is operated under reflux conditions, this sublimate is recovered and returned to the pyrolysis vessel.

Urea sublimation can be significantly reduced by performing the pyrolysis at a higher pressure, such as 760 torr (1 atmosphere). However, the reaction is not quite driven as quickly to completion and the final product is generally found to have a slightly higher level of ammelide or ammeline than is found in subatmospheric pressure operation. Superatmospheric (i.e. greater than 760 torr) operation continues the trends noted above in that urea sublimation is essentially eliminated while ammonia removal is less complete. As a result, the ammeline and ammelide impurity levels are higher than with atmospheric operation and may reach a level where a conventional acid hydrolysis operation may be required to remove them.

Where the cyanuric acid is intended as feedstock for subsequent chlorination reactions to produce products such as sodium dichlorocyanuric acid or trichlorocyanuric acid, lower levels (i.e. about 1 percent or less) of ammelide and ammeline do not present a significant quality problem since this treatment causes them to eliminate the amine groups and replace them with carbonyl oxygen so that the same end product is made but with some $NCl_3$ also being given off. Since it is desired to minimize such $NCl_3$ production, lower pressure operation is preferred, with a 250–350 torr reaction pressure being especially preferred.

At the conclusion of the pyrolysis, the reaction mass of crude cyanuric acid suspended in liquid adiponitrile is maintained under an inert gas such as nitrogen for a post-reaction time of from about 5 to about 30 minutes. This allows the final pyrolysis of any unreacted urea present after which the somewhat cooled cyanuric acid suspensate can be separated easily from the liquid adiponitrile. The separated cyanuric acid crystals can then be washed with a suitable solvent to remove any traces of the adiponitrile and any other impurities remaining on the cyanuric acid. The final cyanuric acid product is generally at least 99 percent pure with any ammelide or ammeline being present in amounts considerably less than 1 percent by weight.

The recovery of the crude cyanuric acid from the reaction mass and its subsequent purification can be performed by a variety of methods. One such method, illustrated in FIG. 1, is filtration of the reaction mass on filter 12 to produce a crude cyanuric acid filter cake and an adiponitrile filtrate. The filter cake can be vacuum dried with a small amount of adiponitrile being recovered or it can be dried with superheated steam. Also, it can be washed with a solvent in which cyanuric acid has only limited solubility but in which adiponitrile is quite soluble. Suitable solvents include methanol, acetone, methyl ethyl ketone, chloroform and similar materials. After washing, the purified filter cake is dried at a nominal temperature.

The solvent wash is evaporated for recovery with any pot residues being combined with the main adiponitrile filtrate. This can be vacuum distilled at approximately 150° C. at 1 torr in still 14 to recover the adiponitrile in a nominally pure form or, if the color of the filtrate is a light yellow (which is essentially that of unreacted adiponitrile), recycled directly back into the urea pyrolysis vessel for further use. Total adiponitrile recovery is generally in the range of 97–99 percent. The pot residue from distillation comprises primarily a small residue of cyanuric acid mixed with some small amount of urea-adiponitrile condensation products primarily 2,4-dihydroxy-6-cyanobutyl-s-triazine and various "color bodies" or tars.

If desired, color bodies in the cyanuric acid product or the pot residue can be substantially removed or destroyed by a simple bleaching treatment with aqueous chlorine, a chloroisocyanurate or an inorganic hypochlorite to provide a purified cyanuric acid which is virtually pure white. The ability to essentially completely remove such color bodies is an unexpected and surprising result of the process of this invention.

FIG. 2 shows a second embodiment for recovering the cyanuric acid from the pyrolysis step. In this case, the reaction mass from pyrolysis step 10 is cooled by feeding to quench vessel 16 containing water at ambient temperature. This cooled diluted slurry is then filtered in filter 12 with the separated filter cake being washed with an additional amount of water to further remove any retained adiponitrile and/or soluble impurities, and, if desired, dried at about 100° C. in dryer 20.

Due to the limited solubility of adiponitrile in water, the filtrate forms a two-phase system; an aqueous phase and an organic phase, which are separated for further treatment. The water in the aqueous phase can be recycled or evaporated in evaporator 18 to leave a pot residue consisting primarily of a small amount of liquid adiponitrile and solid cyanuric acid. This pot residue is filtered and washed in filtration step 22 and dried in dryer 20 in the same manner as described above to recover the cyanuric acid. The adiponitrile filtrate is added to the organic phase which is then distilled in still 14 to recover the adiponitrile as hereinabove described. In this process, adiponitrile recovery is about 98 to 99 percent.

FIG. 3 shows a third embodiment of the subject invention. In this, the cyanuric acid slurry is directly distilled under vacuum in vacuum dryer 24 to recover the adiponitrile, and leaves a pot residue comprised of crude cyanuric acid and other reaction products. This residue may be mixed with a suitable extraction solvent such as those described above to dissolve and remove these impurities and filtered in filtration step 12 as described above. However, with the normally low by-product content produced by the process of the invention, it is usually quite practical to use the crude product directly as a feed for the subsequent production of chloroisocyanurates.

The highly selective nature of the present process in producing cyanuric acid containing minimum amounts of impurities is extremely important in commercial manufacture. The very low levels (<1 percent) of amide impurities obviates the need for digesting the present cyanuric acid product in concentrated mineral acid to hydrolyze them to cyanuric acid. Since this digestion step is a relatively long procedure, requiring several hours, and further since it requires special, acid resistant holding tanks and centrifuges to hold the acid back and separate the digested cyanuric acid from the mineral acid, the process of this invention has a marked advantage over many prior art processes by eliminating this costly and time-consuming operation.

The use of adiponitrile as a solvent for this reaction offers a further economic advantage over prior art processes in that the quantities required for industrial application are readily available at considerably lower prices than most, if not all, of the solvents described in the prior art.

The following examples are given to illustrate the invention and are not deemed to be limiting thereof. All parts and percentages are by weight unless otherwise specified.

EXAMPLES

A summary of the experimental results achieved with six different embodiments of the subject invention is given in Tables I and II below. For most of the examples illustrated, the following pyrolysis conditions prevail:

| Reactor Charge | |
|---|---|
| Adiponitrile | 360–390 grams |
| Urea Prills | 270 grams |
| Average Urea Addition Time | 1.5 hours |
| Temperature Range | 225–230° C. |
| Average Post-Reaction Time | 0.3 hours |
| $NH_3$ Purged During Urea Addition | |
| $N_2$ Cover During Post-Reaction Period | |

In each case, the reactor was heated by a mantle-type heater and moderate agitation was used. $NH_3$ formed by the urea condensation reaction was continuously vented along with some $CO_2$. There was also an observable loss of urea by sublimation. In the examples shown in Tables I and II, the sublimation "loss" ranged from about 5 to about 9 percent of the charged materials which tended to lower slightly the effective yields shown for each run. In a production operation, it is expected that the sublimate would be recovered and returned to the pyrolysis vessel so that losses by sublimation would be eliminated. The cyanuric acid dissolved in the various solvent streams would also be recovered as usable product.

TABLE I

Low Pressure Pyrolysis Of Urea In Adiponitrile

| Example | Reactor[a] | Pressure Torr | Work-Up[b] | Product[c] g | Yield % | Initial Color | % Ammelide and Ammeline |
|---|---|---|---|---|---|---|---|
| 1 | Glass | 300 | F (FIG. 1) | 248[e] | 94 | Dark yellow | |
| 2 | Glass | 300 | F | 176 | 91 | Tan yellow | 0.54 |
| 3 | Glass | 300 | F | 177 | 91 | Brown yellow | 0.46 |
| 4 | 316 SS | 300 | F | 258[e] | 97 | Brown yellow | |
| 5 | Glass | 300 | Q (FIG. 2) | 145[f] | 75 | Yellow | |
| 6 | Glass | 300 | Q | 176 | 91 | Light tan | |
| 7 | Glass | 300 | Q | 166 | 86 | Off-white | |
| 8 | Glass | 300 | Q | 162 | 84 | Tan yellow | 0.66 |
| 9 | 316 SS | 300 | D (FIG. 3) | 173 | 89 | Yellow | 0.30 |
| 10 | Glass | 300 | D | 185 | 96 | Yellow | 0.69 |
| 11 | Glass | 300 | D | 145[d] | 99 | Yellow | 0.61 |

[a]Glass reactor was a 2-L spherical unbaffled flask. 316 SS reactor was a 1.5-L unbaffled resin kettle. Moderate agitation was used. Heat was supplied by a mantle.
[b]F: Product isolated by filtration through coarse frit after cooling to room temperature; filter cake was washed with $CHCl_3$ as shown in FIG. 1.
Q: Hot reactor slurry was poured into 400 g of room temperature $H_2O$, stirring was continued 30 minutes after cooling to 52° C. Slurry was filtered and cake washed with $H_2O$ (3 × 100 g). Product was oven-dried at 100° C. as shown in FIG. 2.
D: Adiponitrile distilled from reaction slurry at reduced pressure (~1 torr) either directly from reactor or after transferring slurry to rotary evaporator. Products were acetone washed to remove residual adiponitrile and solvent by-products as shown in FIG. 3.
[c]In-hand yield, does not include losses of cyanuric acid in wash residues and urea sublimation. If this is included, total yield reaches approximately 97 percent.
[d]Reactor charge: urea 205 g, adiponitrile 278 g.
[e]370 g of urea used.
[f]Low yield due to accidental product loss.

TABLE II
Atmospheric Pressure Pyrolysis Of Urea In Adiponitrile

| Example | Reactor[a] | Pressure Torr | Work-Up[b] | Product[c] g | Yield % | Initial Color | % Ammelide and Ammeline |
|---|---|---|---|---|---|---|---|
| 12 | 316 SS | 760 | F | 169 | 87 | Yellow | |
| 13 | Glass | 760 | Q | 168 | 86 | Off-white | 2.3 |
| 14 | 316 SS | 760 | Q | 148 | 76 | Tan | 1.55 |
| 15 | 316 SS | 760 | D | 325[d] | 84 | Brown | 2.3 |
| 16 | 316 SS | 760 | D | 356[d] | 92 | Yellow | |

[a], [b], [c] See Table I
[d] Double normal reaction charge used.

EXAMPLES 11a–11c

The yellow cyanuric acid obtained in Example 11 was divided into three samples, identified as Samples 11a, 11b and 11c, respectively. A portion of Sample 11a was analyzed for color on a Photovolt Reflectance Meter, in which magnesium oxide has a color value of 100 and was found to have a color value of 15. The remainder of Sample 11a was bleached by digesting in aqueous chlorine, filtered and dried. The bleached cyanuric acid had a color value of 85. Since commercial cyanuric acid generally has a color value ranging from about 55–75, the bleached cyanuric acid of Sample 11a had a color value superior to commercial cyanuric acid.

Sample 11b (yellow cyanuric acid) was converted to monosodium cyanurate and chlorinated in accordance with the procedure of U.S. Pat. No. 3,835,135 which issued Sept. 10, 1974 to Duane L. Sawhill to produce trichloroisocyanuric acid. The color value of the trichloroisocyanuric acid product was 93.

Sample 11c (yellow cyanuric acid) was reacted with trichloroisocyanuric acid from Sample 11b and sodium hydroxide in accordance with the process of U.S. Pat. No. 4,099,005, which issued July 4, 1978 to Fullington et al, to produce sodium dichloroisocyanurate which was found to have a color value of 89. The procedure for bleaching Samples 11a, 11b and 11c represent Examples 11a, 11b and 11c, respectively.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. In a process for making cyanuric acid by pyrolyzing a nitrogenous containing material capable of yielding a cyanuric acid product, said material being dissolved in an inert solvent in a pyrolysis vessel to produce a hot reaction mass comprising a slurry of crude cyanuric acid in said solvent, characterized by the improvement which comprises employing as said solvent a linear alkyl dinitrile of the general formula:

$$N\equiv C(CH_2)_nC\equiv N$$

wherein n ranges from 1 to 8.

2. The process of claim 1 wherein said nitrile solvent further comprises the monomethyl derivatives thereof.

3. The process of claim 1 wherein said solvent is adiponitrile.

4. The process according to claim 1 further comprising steps of removing said reaction mass from said pyrolysis vessel and separating solid cyanuric acid from said alkyl dinitrile solvent in said slurry and returning said solvent to the pyrolysis vessel.

5. The process according to claim 4 wherein said cyanuric acid is separated from said solvent to form a filter cake and a solvent filtrate and heating the resulting cyanuric acid filter cake to dryness.

6. The process according to claim 5 wherein said solvent filtrate is distilled to remove impurities prior to returning it to the pyrolysis vessel.

7. The process according to claim 1 wherein said slurry is quenched in cold water, the resulting cooled slurry being filtered to yield a first filtrate and a cyanuric acid filter cake, said filtrate being comprised of an aqueous phase and an organic phase, separating said phases, distilling said aqueous phase to remove the water and yield a pot residue of cyanuric acid in said solvent, separating said cyanuric acid from said solvent in said pot residue, admixing the clarified pot residue with the organic phase, said organic phase then being distilled to recover the adiponitrile therefrom and admixing the separated cyanuric acid with said filter cake and washing the resulting mixture whereby a purified cyanuric acid product is obtained.

8. The process according to claim 1 wherein said reaction mass is distilled to remove said solvent, leaving a pot residue of crude cyanuric acid, and washing said pot residue to remove impurities whereby a purified cyanuric acid product is obtained.

9. The process according to claim 8 wherein said washing comprises admixing said pot residue in a solvent for said nitrile, separating cyanuric acid from the resulting mixture and recovering the solvent from the resulting liquid phase whereby purified cyanuric acid and nitrile products are obtained.

10. The process according to claim 1 wherein said pyrolysis vessel is maintained below atmospheric pressure during the addition of said nitrogenous containing material.

11. The process according to claim 10 wherein the pressure within the pyrolysis vessel is 250–350 torr.

12. The process according to claim 1 wherein said pyrolysis vessel is maintained at atmospheric pressure.

13. The process according to claim 1 wherein said pyrolysis vessel is maintained above atmospheric pressure during the addition of said nitrogenous containing material.

14. A process for making cyanuric acid comprising:
pyrolyzing in a pyrolysis vessel at a temperature of about 200° C. to 250° C., a solution of urea in adiponitrile to produce a slurry of crude cyanuric acid in adiponitrile;
removing said slurry from said vessel and filtering said slurry to produce a cyanuric acid filter cake and an adiponitrile filtrate;

returning said adiponitrile to said pyrolysis vessel and washing said filter cake to remove soluble impurities whereby a purified cyanuric acid product is obtained.

15. The process according to claim 14 wherein said adiponitrile is distilled to remove dissolved impurities prior to its being returned to said pyrolysis vessel.

16. A process for making cyanuric acid comprising:
pyrolyzing in a pyrolysis vessel at a temperature of about 200° C. to 250° C., a solution of urea in adiponitrile to produce a slurry of crude cyanuric acid in adiponitrile;
removing said slurry from said vessel and quenching it in room temperature water;
filtering said quenched slurry to remove said cyanuric acid as a filter cake from a separable mixture of water and a first adiponitrile filtrate;
separating said water from said adiponitrile and evaporating said water to produce a pot residue of cyanuric acid and adiponitrile;
filtering said pot residue to recover said cyanuric acid from said adiponitrile, said adiponitrile being admixed with said first adiponitrile filtrate;
distilling said combined filtrates to produce a purified adiponitrile to be returned to the pyrolysis vessel; and
combining said recovered cyanuric acid residue with said filter cake and washing said combination to remove soluble impurities whereby a purified cyanuric acid product is obtained.

17. A process for making cyanuric acid comprising:
pyrolyzing in a pyrolysis vessel at a temperature of about 200° C. to 250° C., a solution of urea in adiponitrile to produce a slurry of crude cyanuric acid in adiponitrile;
removing said slurry and distilling it to remove said adiponitrile and leave a crude cyanuric acid as a pot residue;
washing said pot residue to remove impurities with a solvent whereby a purified cyanuric acid product is obtained.

18. The process according to claims 14, 16, or 17 wherein said pyrolysis vessel is held at a pressure of 0–350 torr.

19. The process according to claims 14, 16, or 17 wherein said pyrolysis vessel is held at atmospheric pressure.

20. The process according to claims 14, 16, or 17 wherein said pyrolysis vessel is held at a pressure in excess of atmospheric pressure.

21. The process according to claims 1, 14, 16 or 17 further comprising the step of bleaching said cyanuric acid product to remove color bodies in said product.

22. The process of claim 21 wherein said bleaching step is performed with an aqueous solution of chlorine.

23. The process of claim 1 wherein the nitrogenous containing material is urea.

* * * * *

UNITED STATES PATENT AND TRADEMARK OFFICE
CERTIFICATE OF CORRECTION

PATENT NO. : 4,360,671

DATED : November 23, 1982

INVENTOR(S) : John A. Wojtowicz and Douglas A. Farmer, Jr.

It is certified that error appears in the above-identified patent and that said Letters Patent is hereby corrected as shown below:

Column 2, line 53, "'to" should read --1 to--.

Column 4, line 53, "2,4-dihydroxy-6-cyanobutyl-s-triazine" should read --2,4-dihydroxy-6-cyanobutyl-s-triazine--.

Signed and Sealed this

First Day of November 1983

[SEAL]

Attest:

Attesting Officer

GERALD J. MOSSINGHOFF

Commissioner of Patents and Trademarks